United States Patent
Sabesan et al.

(10) Patent No.: US 8,715,969 B2
(45) Date of Patent: May 6, 2014

(54) DELIGNIFICATION OF BIOMASS WITH SEQUENTIAL BASE TREATMENT

(75) Inventors: Subramaniam Sabesan, Wilmington, DE (US); Christina Jacy Spado, Philadelphia, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 384 days.

(21) Appl. No.: 12/621,599

(22) Filed: Nov. 19, 2009

(65) Prior Publication Data

US 2010/0124771 A1    May 20, 2010

Related U.S. Application Data

(60) Provisional application No. 61/116,386, filed on Nov. 20, 2008, provisional application No. 61/116,382, filed on Nov. 20, 2008, provisional application No. 61/116,388, filed on Nov. 20, 2008, provisional application No. 61/116,378, filed on Nov. 20, 2008.

(51) Int. Cl.
| | |
|---|---|
| C07H 1/08 | (2006.01) |
| C08B 37/00 | (2006.01) |
| C13K 1/02 | (2006.01) |
| C13K 1/04 | (2006.01) |
| C08B 37/08 | (2006.01) |
| C08B 37/14 | (2006.01) |

(52) U.S. Cl.
CPC ............... *C08B 37/00* (2013.01); *C08B 37/003* (2013.01); *C08B 37/0033* (2013.01); *C08B 37/14* (2013.01)
USPC ............. 435/128; 435/42; 435/100; 435/105; 127/37; 127/46.1

(58) Field of Classification Search
None
See application file for complete search history.

(56) References Cited

U.S. PATENT DOCUMENTS

| 975,387 A | 11/1910 | Hutchinson |
| 1,887,241 A | 11/1932 | Hooper |
| (Continued) | | |

FOREIGN PATENT DOCUMENTS

| GB | 1434232 | 5/1976 |
| WO | 0237981 A2 | 5/2002 |
| WO | 03031348 A2 | 4/2003 |

OTHER PUBLICATIONS

Parthasarathy, V. R., Bleaching of nonwood pulps: can sodium hydroxide be replaced with sodium carbonate in the alkaline extraction of nonwood pulps?, Tappi Journal, Aug. 1991, pp. 183-186.

*Primary Examiner* — Karen Cochrane Carlson
*Assistant Examiner* — William W Moore

(57) ABSTRACT

A method for the production of a saccharification product is provided, the method comprising:
  a) providing a cellulosic feedstock comprising lignin;
  b) contacting, in water, the feedstock of (a) with at least one metal carbonate at time 0 hour under suitable initial reaction conditions to produce a first delignification slurry;
  c) contacting the first delignification slurry with a nucleophilic base at time (0+n) hour, where n represents a number greater than zero, under suitable secondary reaction conditions to form a second delignification slurry comprising a lignin-containing liquid fraction and a polysaccharide-enriched solid fraction;
  d) separating the lignin-containing liquid fraction from the polysaccharide-enriched solid fraction; and
  e) contacting at least a portion of the polysaccharide-enriched solid fraction with an enzyme consortium to produce a saccharification product comprising xylose and glucose monomers wherein the overall yield of xylose and glucose monomers in the saccharification product are individually at least about 50%.

11 Claims, 1 Drawing Sheet

(56) References Cited

U.S. PATENT DOCUMENTS

| | | | |
|---|---|---|---|
| 3,944,463 A | 3/1976 | Samuelson et al. | |
| 4,089,737 A | 5/1978 | Nagano et al. | |
| 4,609,624 A * | 9/1986 | Rothlisberger | 435/157 |
| 6,908,995 B2 * | 6/2005 | Blount | 536/123 |
| 8,304,535 B2 * | 11/2012 | Harmer et al. | 536/128 |
| 8,372,609 B2 * | 2/2013 | Sabesan | 435/132 |
| 8,524,474 B2 * | 9/2013 | Sabesan et al. | 435/165 |
| 2004/0121436 A1 | 6/2004 | Blount | |
| 2007/0031918 A1 * | 2/2007 | Dunson et al. | 435/41 |
| 2009/0145021 A1 * | 6/2009 | Guay et al. | 44/307 |
| 2010/0124770 A1 * | 5/2010 | Sabesan et al. | 435/101 |
| 2010/0124772 A1 * | 5/2010 | Sabesan | 435/105 |
| 2010/0125135 A1 * | 5/2010 | Harmer et al. | 536/123.1 |
| 2010/0143974 A1 * | 6/2010 | Chung et al. | 435/72 |

\* cited by examiner

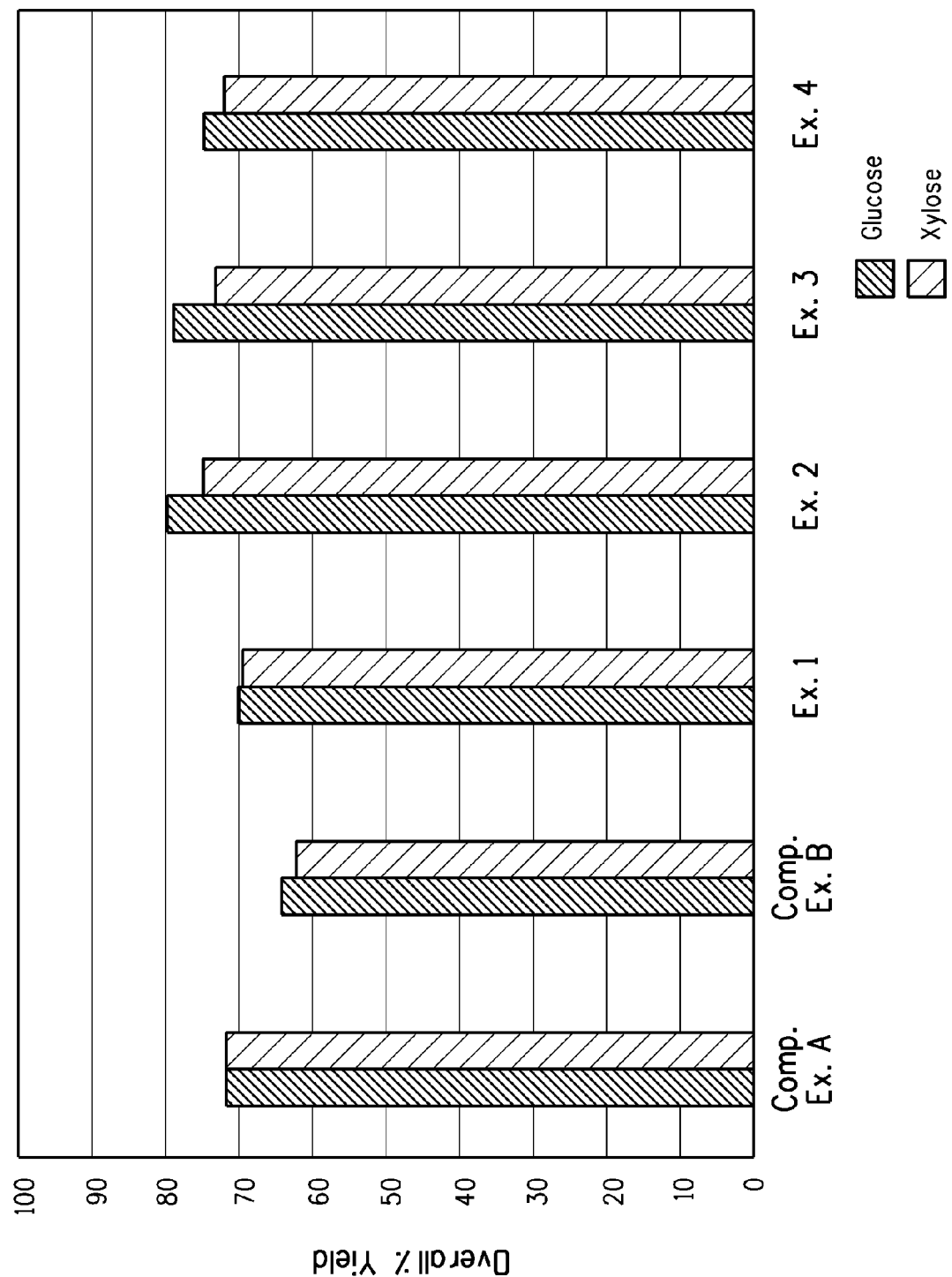

DELIGNIFICATION OF BIOMASS WITH SEQUENTIAL BASE TREATMENT

CROSS-REFERENCE TO RELATED APPLICATIONS

This application claims the benefit of U.S. Provisional Application No. 61/116,382 filed Nov. 20, 2008, U.S. Provisional Application No. 61/116,386 filed Nov. 20, 2008, U.S. Provisional Application No. 61/116,388 filed Nov. 20, 2008 and U.S. Provisional Application 61/116,378, filed Nov. 20, 2008. This application hereby incorporates by reference Provisional Application Nos. 61/116,382, 61/116,388, 61/116,378, and 61/116,386 in their entirety.

FIELD OF THE INVENTION

Methods for delignifying biomass and preserving sugar yield through saccharification are provided. Specifically, polysaccharide-enriched biomass may be obtained by the sequential pretreatment of a cellulosic feedstock with at least one metal carbonate followed by a nucleophilic base. A saccharification product comprising xylose and glucose monomers may be obtained by enzymatic saccharification of the polysaccharide-enriched biomass.

BACKGROUND

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as fuels and other chemicals. Cellulosic and lignocellulosic feedstocks and wastes, composed of carbohydrate polymers comprising cellulose, hemicellulose, and lignin are generally treated by a variety of chemical, mechanical and enzymatic means to release primarily hexose and pentose sugars, which can then be fermented to useful products.

Pretreatment methods are used to make the carbohydrate polymers of cellulosic and lignocellulosic materials more readily available to saccharification enzymes. Standard pretreatment methods have historically utilized primarily strong acids at high temperatures; however due to high energy costs, high equipment costs, high pretreatment catalyst recovery costs and incompatibility with saccharification enzymes, alternative methods are being developed, such as enzymatic pretreatment, or the use of acid or base at milder temperatures where decreased hydrolysis of biomass carbohydrate polymers occurs during pretreatment, requiring improved enzyme systems to saccharify both cellulose and hemicellulose.

U.S. Pat. No. 975,387 relates to a process of treating bagasse with the object to separate therefrom a maximum portion of its papermaking contents with the least expense of materials and time and of a quality suitable for making a commercially useful bagasse paper. The patent discloses that in carrying out the preferred process in which the first main stage thereof comprises two digestive treatments, i.e. fractional digestion, the bagasse is placed in the receptacle and treated for about thirty minutes with a solution containing about from 2.5 to 5 percent of sodium carbonate at about 100° C. or up to and under a steam pressure of ten pounds. The liquid is then run off and the charge is further treated for about 30 minutes with a solution of from 5 percent to 7.5 percent of caustic soda at about the same temperature or steam pressure. Between the two stages the material should be washed for the purpose above explained by running water through it.

U.S. Pat. No. 1,887,241 relates to a digesting or cooking process of treating wood chips for the purpose of producing fiber or pulp, said process to consist of more than one stage. The patent discloses the use of a comparatively cheap chemical, sodium carbonate, in weak solution in the first stage, and in the second stage a solution of caustic soda which is weaker than that now commonly used in the "soda process". By so doing, it is possible to obtain a larger yield of pulp, from one to five percent, and a greater economy in the use of chemicals, than has been possible by the usual method of using caustic soda only.

A method for producing sugars is needed which selectively removes only lignin without significant loss of either glucan or xylan from the biomass, as these constitute the source of sugars for fermentation. In order to be economically competitive, a commercial process for the production of sugars from renewably-sourced biomass requires the hydrolysis of carbohydrates in lignocellulosic biomass to provide high yields of sugars. An economic process which provides good yields of sugars such as glucose and xylose through both delignification and saccharification is desired. Further desired is a process which provides a saccharification product in good yield and with reduced use of costly pretreatment ingredients, such as sodium hydroxide. Additionally, recycling at least a portion of the chemical waste produced from pretreatment of biomass would be desired.

SUMMARY

Described herein are methods to produce a saccharification product comprising xylose and glucose monomers by sequential pretreatment of a cellulosic feedstock with base, followed by enzymatic saccharification. The described methods involve pretreatment steps wherein a cellulosic feedstock comprising lignin is contacted in water with at least one metal carbonate to produce a first delignification slurry, followed by contacting the first delignification slurry with a nucleophilic base to form a second delignification slurry. During pretreatment, the lignin is selectively solubilized and both glucan and xylan are essentially retained in the resulting solid polysaccharide-enriched biomass. The metal carbonate may be recyclable. The polysaccharide-enriched biomass is then contacted with an enzyme consortium to produce a saccharification product comprising xylose and glucose monomers.

In one embodiment a method for the production of a saccharification product is described, the method comprising:

a) providing a cellulosic feedstock comprising lignin;
b) contacting, in water, the feedstock of (a) with at least one metal carbonate at time 0 hour under suitable initial reaction conditions to produce a first delignification slurry;
c) contacting the first delignification slurry with a nucleophilic base at time (0+n) hour, where n represents a number greater than zero, under suitable secondary reaction conditions to form a second delignification slurry comprising a lignin-containing liquid fraction and a polysaccharide-enriched solid fraction;
d) separating the lignin-containing liquid fraction from the polysaccharide-enriched solid fraction; and
e) contacting at least a portion of the polysaccharide-enriched solid fraction with an enzyme consortium to produce a saccharification product comprising xylose and glucose monomers wherein the overall yield of xylose and glucose monomers in the saccharification product are individually at least about 50%.

In one embodiment, the metal carbonate may be selected from the group consisting of lithium carbonate, sodium carbonate, potassium carbonate, cesium carbonate, magnesium carbonate, ammonium carbonate, and combinations thereof. The initial reaction conditions may include an initial pH range from about 9.0 to about 11.0 and a reaction temperature of about 30° C. to about 200° C.

According the methods of the invention, the lignin-containing liquid fraction may be pyrolyzed to form a metal carbonate-containing ash. The metal carbonate of step (b) may be supplied by the metal carbonate-containing ash.

In one embodiment, the nucleophilic base comprises a soluble metal hydroxide. The nucleophilic base may be selected from the group consisting of lithium hydroxide, sodium hydroxide, potassium hydroxide, cesium hydroxide, magnesium hydroxide, and combinations thereof. The secondary reaction conditions may include a reaction temperature of about 25° C. to about 200° C. In one embodiment, the value of n may be between 0.5 and 20 inclusive. In one embodiment, the ratio of the concentration of nucleophilic base to the concentration of metal carbonate in the second delignification slurry of step (c) may be from about 0.1:1 to about 1.0:1 on a weight basis.

In one embodiment, the cellulosic feedstock may be selected from the group consisting of switchgrass, corn grain, corn cobs, corn husks, corn stover, grasses, wheat, wheat straw, hay, barley, barley straw, rice straw, sugar cane bagasse, sorghum, soy, components obtained from processing of grains, trees, branches, roots, leaves, wood chips, sawdust, shrubs and bushes, vegetables, fruits, flowers, and animal manure, and a combination of these.

According to the methods of the invention, the saccharification enzyme consortium may comprise at least one enzyme selected from the group consisting of cellulose-hydrolyzing glycosidases, hemicellulose-hydrolyzing glycosidases, starch-hydrolyzing glycosidases, peptidases, lipases, ligninases, and feruloyl esterases. In one embodiment, the saccharification enzyme consortium may comprise at least one enzyme selected from the group consisting of cellulases, endoglucanases, exoglucanases, cellobiohydrolases, β-glucosidases, xylanases, endoxylanases, exoxylanases, β-xylosidases, arabinoxylanases, mannases, galactases, pectinases, glucuronidases, amylases, α-amylases, β-amylases, glucoamylases, α-glucosidases, and isoamylases. The saccharification pH may be from about 4.5 to about 5.7.

BRIEF DESCRIPTION OF THE FIGURE

The methods described herein are described with reference to the following figure.

FIG. 1 is a graphical representation of the overall yields of glucose and xylose monomers through the delignification and saccharification steps of Comparative Examples A and B, and Examples 1, 2, 3, and 4.

DETAILED DESCRIPTION OF THE INVENTION

Definitions

The methods described herein are described with reference to the following terms.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "invention" or "present invention" as used herein is a non-limiting term and is not intended to refer to any single variation of the particular invention but encompasses all possible variations described in the specification and recited in the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid.

As used herein, biomass may also be referred to as "a cellulosic feedstock comprising lignin".

As used herein, the term "lignocellulosic" refers to a composition comprising both lignin and cellulose. Lignocellulosic material may also comprise hemicellulose.

As used herein, the term "cellulosic" refers to a composition comprising cellulose.

As used herein, by "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

As used herein, the terms "target chemical" and "target product" are interchangeable and refer to a chemical, fuel, or chemical building block produced by fermentation. Chemical or product is used in a broad sense and includes molecules such as proteins, including, for example, peptides, enzymes, and antibodies. Also contemplated within the definition of target product are ethanol and butanol.

As used herein, the term "saccharification" refers to the hydrolysis of polysaccharides to their constituent monomers and/or oligomers.

As used herein, the term "polysaccharide-enriched biomass" means biomass that has been subjected to pretreatment prior to saccharification such that the noncarbohydrate component of the biomass is significantly reduced.

As used herein, "readily saccharifiable biomass" means biomass that is carbohydrate-enriched and made more amenable to hydrolysis by cellulolytic or hemi-cellulolytic enzymes for producing monomeric and oligomeric sugars. The term "readily saccharifiable biomass" as used herein is interchangeable with the term "solid fraction of the polysaccharide-enriched biomass".

As used herein, the term "carbohydrate-enriched" as used herein refers to the biomass produced by the process treatments described herein. The terms polysaccharide-enriched and carbohydrate-enriched are interchangeable.

As used herein, the term "loading of the enzyme consortium" and "enzyme loading" are interchangeable and refer to a ratio of the amount total weight of protein in the enzyme consortium relative to the weight of polysaccharide enriched biomass.

As used herein, the terms "delignification" refers to any process by which lignin is either partly, mostly or wholly removed from cellulosic materials. Generally, this process is by means of chemical treatment. The residue that remains consists of cellulose, hemicelluloses, and other carbohydrate materials. Any residue having undergone a delignification is described herein as "delignified". As used herein, "lignin" refers generally to a polymer found extensively in the cell walls of all woody plants.

As used herein, the term "cellulase" refers to polysaccharide-hydrolyzing enzymes that can exhibit an activity, such as cellulose degradation, that may be several enzymes or a group of enzymes having different substrate specificities. Thus, a cellulase from a microorganism may comprise a group of enzymes, all of which may contribute to the cellulose-degrading activity.

As used herein, the terms "nucleophile" and "nucleophilic base" refer to a Lewis base (as that term is used in the art) that is a reagent that forms a chemical bond to its reaction partner, the electrophile, by donating both bonding electrons. Most bases are also nucleophiles. (See for example *Organic Chemistry*, 7$^{th}$ Edition, Morrison, Robert Thornton; Boyd, Robert N., (1998) Publisher: (Prentice Hall, Englewood Cliffs, N.J.). For example, in the methods described herein, the nucleophile NaOH reacts and forms chemical bonds with lignin and its components.

Sequential Pretreatment with Base (Delignification)

In the methods described herein, a cellulosic feedstock comprising lignin is contacted in water with at least one metal carbonate at time 0 hour under suitable initial reaction conditions to produce a first delignification slurry, which is then contacted with a nucleophilic base at time (0+n) hour, where n represents a number greater than zero, under suitable secondary reaction conditions to form a second delignification slurry comprising a lignin-containing liquid fraction and a polysaccharide-enriched solid fraction. The polysaccharide-enriched solid fraction is separated from the lignin-containing liquid fraction and contacted with an enzyme consortium to produce a saccharification product comprising xylose and glucose monomers wherein the overall yield of xylose and glucose monomers in the saccharification product are individually at least about 50%.

The source of the cellulosic feedstock is not determinative of the invention and the biomass may be from any source. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof. Biomass that is useful for the invention may include biomass that has a relatively high carbohydrate value, is relatively dense, and/or is relatively easy to collect, transport, store and/or handle. In one embodiment of the invention, biomass that is useful includes corn cobs, corn stover, sawdust, and sugar cane bagasse.

The cellulosic feedstock comprising lignin may be used directly as obtained from the source, or energy may be applied to the biomass to reduce the size, decrease the crystallinity of cellulose in the biomass, increase the exposed surface area, and/or increase the availability of cellulose, hemicellulose, and/or oligosaccharides present in the biomass to the metal carbonate, to the nucleophilic base, and to the saccharification enzymes used in the saccharification step. Energy means useful for reducing the size, decrease the crystallinity of cellulose in the biomass, increasing the exposed surface area, and/or increasing the availability of cellulose, hemicellulose, and/or oligosaccharides present in the cellulosic feedstock include, but are not limited to, milling, crushing, grinding, shredding, chopping, disc refining, ultrasound, and microwave. This application of energy may occur before or during pretreatment, before and during saccharification, or any combination thereof.

In general, it is often required to mill the biomass before and/or after pretreatments in order to reduce the particle size and to produce high surface area and porous particles for effective enzymatic saccharification. In the current invention, we unexpectedly find that this energy intensive milling process can be avoided, as the sequential base treatment under selected conditions results in chemical milling to provide delignified biomass of substantially reduced particle size.

The cellulosic feedstock is contacted, in water, with at least one metal carbonate at time 0 hour. The metal carbonate may be selected from the group consisting of lithium carbonate, sodium carbonate, potassium carbonate, cesium carbonate, magnesium carbonate, ammonium carbonate, and combinations thereof. Metal bicarbonates may also be used, alone or in combination with at least one metal carbonate. The metal carbonate may be combined as an aqueous solution or as a solid with the cellulosic feedstock and water to form a first delignification slurry having an initial pH of about 9.0 to about 11.0. As the delignification proceeds, some of the base is consumed and the pH of the biomass slurry is reduced. A sufficient concentration of base should be used such that the pH does not drop below about 9.0, which would result in insufficient delignification.

Suitable initial reaction conditions to produce a first delignification slurry may also include a reaction temperature of about 30° C. to about 200° C. The reaction temperature may be from about 70° C. to about 150° C.

In the methods described herein, the solids loading, or ratio of solid to liquid, in the first delignification slurry may be from about 0.1:1 to about 1:1 on a weight basis. When expressed as a percentage, the solids loading may typically be from about 5% to about 50%, for example from about 10% to about 30%. Useful ranges of solids loading are dependent on the viscosity of the first delignification slurry, and may be affected by the type of biomass used and the particle size, for example. The biomass concentration may be maximized to the extent possible to minimize the volume of the reaction vessel. The high biomass concentration also reduces the total volume of pretreatment material, making the process more economical. From a practical viewpoint, high ratios of the weight of biomass to the weight of the basic solution may be limited by the ability to provide sufficient mixing, or intimate contact, for pretreatment to occur at a practical rate.

The contacting of the cellulosic feedstock with water and at least one metal carbonate may be carried out for a period of time expressed as time (0+n) hour, where n represents a number greater than zero. The contacting may be from a fraction of an hour, such as a few seconds (e.g. n is at least 0.001 using hour as the unit of time) to about 24 hours (e.g. n=24). Longer periods of contacting with at least one metal carbonate are possible, however a shorter period of time may be preferable for practical, economic reasons. Typically a period of contact may be from about 0.5 hours to about 20 hours, which may be represented as a contact time (0+n) wherein the value of n is between 0.5 and 20 inclusive. Typically, the pH of the first delignification slurry remains steady when the contact time has been sufficient. At the end of the contact time, the time (0+n) hour assumes a second meaning and represents the time at which the first delignification slurry is contacted with a nucleophilic base.

The contacting of the cellulosic feedstock with at least one metal carbonate may be performed at a relatively high temperature for a relatively short period of time, for example at about 100° C. to about 200° C. for about 4 hours to about 0.5 hours. Alternatively, the contacting with at least one metal carbonate may be performed at a lower temperature for a longer period of time, for example from about 30° C. to about 95° C. for about 200 hours to about 8 hours. Other temperature and time combinations intermediate to these may also be used.

For the contacting of the cellulosic feedstock with water and at least one metal carbonate, the temperature, reaction time, base concentration, weight percent of water, the biomass concentration, the biomass type, the amount of lignin present, and the biomass particle size are related; thus, these variables may be adjusted as necessary to obtain a sufficient delignification rate in a controllable manner and to obtain an optimal product for contacting with a nucleophilic base at time (0+n) hour.

The first delignification slurry is contacted with a nucleophilic base at time (0+n) hour, where n represents a number greater than zero, under suitable secondary reaction conditions to form a second delignification slurry comprising a lignin-containing liquid fraction and a polysaccharide-enriched solid fraction. The nucleophilic base may comprise a soluble metal hydroxide. The nucleophilic base may be selected from the group consisting of lithium hydroxide, sodium hydroxide, potassium hydroxide, cesium hydroxide, magnesium hydroxide, and combinations thereof. The nucleophilic base may be combined as an aqueous solution or as a solid with the first delignification slurry to form a mixture having an initial pH of about 7 to about 11. As the delignification proceeds, some of the base is consumed and the pH of the mixture is reduced. A sufficient concentration of base should be used such that the pH does not drop below about 9, which would result in insufficient delignification. In the second delignification slurry, the ratio of the concentration of nucleophilic base to the concentration of metal carbonate may be from about 0.1:1 to about 2.0:1 on a weight basis. For example, the ratio may be from about 0.25:1 to about 1:1.

Suitable secondary reaction conditions to form a second delignification slurry further include a reaction temperature of about 25° C. to about 200° C. The secondary reaction temperature may be from about 80° C. to about 120° C.

The contacting of the first delignification slurry with a nucleophilic base starting at time (0+n) hour may be carried out for a period of time from a few minutes to 24 hours. Longer periods of contacting with a nucleophilic base are possible, however a shorter period of time may be preferable for practical, economic reasons. Typically a period of contact may be from about 4 hours to about 24 hours. Typically, the pH remains steady when the contact time has been sufficient to form a second delignification slurry.

The contacting of the first delignification slurry with a nucleophilic base may be performed at a relatively high temperature for a relatively short period of time, for example at about 200° C. to about 150° C. for about 0.5 hours to about 2 hours. Alternatively, the contacting with a nucleophilic base may be performed at a lower temperature for a longer period of time, for example from about 30° C. to about 90° C. for about 200 hours to about 30 hours. Other temperature and time combinations intermediate to these may also be used.

For the contacting of the first delignification slurry with a nucleophilic base, the temperature, reaction time, base concentration, weight percent of water, the biomass concentration, the biomass type, the amount of lignin present, and the biomass particle size are related; thus, these variables may be adjusted as necessary to obtain a sufficient delignification rate in a controllable manner and to obtain an optimal product for saccharification.

The sequential contacting of the cellulosic feedstock with at least one metal carbonate at time 0 hour to produce a first delignification slurry, and the contacting of the first delignification slurry with a nucleophilic base at time (0+n) hour, may be performed in any suitable vessel, such as a batch reactor a continuous reactor. The suitable vessel may be equipped with a means, such as impellers, for agitating the biomass/acid mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, NY). The base treatment steps may be carried out as a batch process, or as a continuous process. In one embodiment, the contacting with at least one metal carbonate may be performed in one vessel, and the first delignification slurry transferred to another vessel for contacting with a nucleophilic base. In one embodiment, the contacting with a nucleophilic base may be performed in the same vessel as the contacting with at least one metal carbonate.

In order to obtain sufficient quantities of sugars from biomass, the biomass may be pretreated sequentially with sodium carbonate and sodium hydroxide either once or several times. Likewise, a saccharification reaction may be performed one or more times. Both pretreatment and saccharification processes may be repeated if desired to obtain higher yields of sugars. To assess performance of the pretreatment and saccharification processes, separately or together, the theoretical yield of sugars derivable from the starting biomass may be determined and compared to the measured yields.

The delignified cellulosic feedstock is referred to as "polysaccharide-enriched biomass" or "carbohydrate-enriched biomass" because the sequential base pretreatment described above, and in more detail below, solubilizes the lignin contained in the biomass. The glucan and xylan remain insoluble. Physical separation of the lignin-containing liquid fraction from the solid fraction removes lignin and provides solid polysaccharide enriched biomass.

Delignifying biomass prior to enzymatic hydrolysis (saccharification) is advantageous as lignin can bind non-specifically to saccharification enzymes. Removal of lignin before saccharification may enable the use of lower enzyme loadings, which provides cost savings with regard to enzyme usage. Removing lignin before saccharification may also improve saccharification rate, titer, and yield. Furthermore, as lignin can contribute to increased viscosity of biomass and biomass slurry, removal of lignin may provide reduced viscosity of biomass and slurries containing biomass, thereby enabling very high loading of the biomass in order to produce concentrated sugar syrup. Delignifying biomass also provides a lignin-containing process stream from which energy value can be obtained through combustion.

Saccharification

Following sequential treatment of the cellulosic feedstock with at least one metal carbonate at time 0 hour and with a nucleophilic base at time (0+n) hour, the second delignification slurry comprises a lignin-containing liquid fraction and a polysaccharide-enriched solid fraction. The second delignification slurry may further comprise a mixture of metal carbonate, nucleophilic base, water, partially degraded biomass, lignin, polysaccharides, and monosaccharides. The solid fraction comprises biomass in which the non-carbohydrate component has been significantly reduced. The liquid fraction is composed of lignin and its fragments as its metal salt, along with the excess base and salts related to the metal carbonate and the nucleophilic base. Prior to saccharification, at least a portion of the solid fraction of the polysaccharide enriched biomass may be isolated in order to physically separate it from the lignin-containing liquid fraction. Isolation of as much of the solid fraction as possible is advantageous, as this allows higher yield of sugars to be obtained after saccharification.

One of the advantages of the present methods is the high selectivity for removing lignin from the biomass while leaving the carbohydrates largely intact. Less selective pretreatment methods hydrolyze a portion of the carbohydrates to sugars which, being more soluble than glucan and xylan, are therefore separated from the carbohydrates (polysaccharides) in the solid isolation step. Removal of some of the monomeric sugars with the lignin in the separation step may result in a decrease in the overall yield to sugar (i.e. through a saccharification step). The present methods minimize monomeric sugar loss during lignin removal, which is of economic benefit.

Methods for separating the solid fraction from the liquid fraction include, but are not limited to, decantation, filtration, and centrifugation. Methods of filtration include, for example, belt filtration, vacuum filtration, and pressure filtration. Optionally, at least a portion of the solid fraction may be recycled to the sequential base pretreatment portion of the process. The solid fraction may optionally be washed with an aqueous solvent (e.g., water) to remove adsorbed lignin prior to being recycled to the sequential base pretreatment portion of the process. The solid fraction may then be re-subjected to additional sequential base treatment as described above, followed by saccharification with a saccharification enzyme consortium.

The liquid fraction containing lignin may optionally be used as an energy source, or some of the desirable components contained in it may be isolated for additional uses. The lignin containing liquid may be concentrated to recover and recycle at least some of the water necessary for the pretreatment process, and the resulting lignin-containing solid may be pyrolyzed at high temperature to generate steam and electricity. The ash obtained from burning the lignin and salts may contain metal carbonates, a portion of which may be recycled to the pretreatment process or may be used as a valuable industrial byproduct. Such metal carbonate recycling may reduce the amount of new metal carbonate required in the pretreatment step, and may thus provide economic benefit.

In the methods described herein, an aqueous suspension of at least a portion of the polysaccharide-enriched solid fraction is contacted with a saccharification enzyme consortium, at a pH and a temperature sufficient to produce a saccharification product comprising xylose and glucose monomers wherein the overall yield of xylose and glucose monomers in the saccharification product are individually at least about 50%. The individual yields of xylose and glucose monomers in the saccharification product may be at least about 55%, 60%, 65%, 70%, 75%, 80%, or higher.

Prior to saccharification, the aqueous suspension of the polysaccharide-enriched solid may be treated to alter the pH, composition or temperature such that the enzymes of the saccharification enzyme consortium will be active. The pH may be altered through the addition of acids in solid or liquid form. Alternatively, carbon dioxide ($CO_2$), which may be recovered from fermentation, may be utilized to lower the pH. For example, $CO_2$ may be collected from a fermenter and fed, such as by bubbling, into the aqueous suspension of the polysaccharide-enriched solid while monitoring the pH, until the desired pH is achieved. The temperature may be brought to a temperature that is compatible with saccharification enzyme activity, as noted below. Any cofactors required for activity of enzymes used in saccharification may be added.

At least a portion of the polysaccharide-enriched solid is then further hydrolyzed in the presence of a saccharification enzyme consortium to release oligosaccharides and/or monosaccharides in a hydrolyzate. Saccharification enzymes and methods for biomass treatment are reviewed in Lynd, L. R., et al. (Microbiol. Mol. Biol. Rev. (2002) 66:506-577).

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

Preferably the saccharification reaction is performed at or near the temperature and pH optima for the saccharification enzymes. The temperature optimum used with the saccharification enzyme consortium in the present method may range from about 15° C. to about 100° C. The temperature optimum may range from about 20° C. to about 80° C., or from about 30° C. to about 60° C., or from about 45° C. to about 55° C. The pH optimum may range from about 4 to about 6 or from about 4.5 to about 5.7.

The saccharification may be performed for a time of about several hours to a few days, for example from about 2 hours to about 3 days. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium. These variables may be adjusted as necessary to obtain an optimal saccharification product for use in fermentation.

The saccharification may be performed batch-wise or as a continuous process. The saccharification may also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The saccharification product comprises xylose and glucose monomers wherein the overall yield of xylose and glucose monomers in the saccharification product are individually at least about 50%. Depending on the cellulosic feedstock used, the saccharification product may further comprise at least one sugar monomer selected from the group consisting of arabinose, mannose, galactose, and a combination thereof.

The saccharification reaction may be performed in any suitable vessel, such as a batch reactor a continuous reactor. The suitable vessel may be equipped with a means, such as impellers, for agitating the biomass/acid mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, NY).

The degree of solubilization of sugars from biomass following saccharification may be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem. (1959) 31:426-428). Alternatively, sugars can be measured by HPLC using an appropriate column as described herein in the General Methods section.

Fermentation to Target Products

The readily saccharifiable biomass produced by the present methods may be hydrolyzed by enzymes as described above to produce fermentable sugars which then may be fermented into a target product. "Fermentation" refers to any fermentation process or any process comprising a fermentation step. Target products include, without limitation alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., Biocommodity Engineering, Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980).

Potential coproducts may also be produced, such as multiple organic products from fermentable carbohydrate. Lignin-rich residues remaining after pretreatment and fermentation may be converted to lignin-derived chemicals, chemical building blocks or used for power production.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, G. P., in *Hand-* book on Bioethanol: Production and Utilization, Wyman, C. E., ed., Taylor & Francis, Washington, D.C., 179-212, 1996). SSCF includes the cofermentation of multiple sugars (Sheehan, J., and Himmel, M., Bioethanol, Biotechnol. Prog. 15: 817-827, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., Microbiol. Mol. Biol. Reviews, 66: 506-577, 2002).

These processes may be used to produce target products from the readily saccharifiable biomass produced by the pretreatment methods described herein.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

The following materials were used in the examples. All commercial reagents were used as received. Sulfuric acid, glucose, xylose, phosphoric acid and citric acid were obtained from Sigma-Aldrich (St. Louis, Mo.). Sodium hydroxide was obtained from EMD Chemicals Inc, (Gibbstown, N.J.). Sodium carbonate was obtained from J. T. Baker (Phillipsburg, N.J.). Polyethylene glycol was obtained from Aldrich (St. Louis, Mo.). The enzymes were obtained from Genencor International, Rochester, N.Y.

Corn cob was purchased from Independence Corn By Products (ICBP Cob), Independence, Iowa. The seller stored the cob at 60° C. and milled and sieved the cob to ⅛". The dry mass content of the cob was about 92.5%. Another variety of cob referred to as MDO7 cob was obtained from University of Wisconsin Farm, in Madison, Wis. and was milled to assorted sizes.

The following abbreviations are used: "HPLC" is High Performance Liquid Chromatography, "C" is Celsius, "mm" is millimeter, "µm" is micrometer, "µL" is microliter, "mL" is milliliter, "L" is liter, "min" is minute, "d" is day(s), "mM" is millimolar, "cm" is centimeter, "g" is gram(s), "mg" is milligrams, "wt" is weight, "wt %" means weight percent, "h" is hour(s), "temp" or "T" is temperature, "DWB" is dry weight of biomass, "Comp. Ex." Is Comparative Example; "NREL" is the abbreviation for "National Renewable Energy Laboratories". "LAP" is the abbreviation for "Laboratory Analytical Procedure".

Carbohydrate Analysis of Biomass

A modified version of the NREL LAP procedure "Determination of Structural Carbohydrates and Lignin in Biomass" was used to determine the weight percent glucan and xylan in the biomass. Sample preparation was simplified by drying at 80° C. under vacuum or at 105° C. under ambient pressure overnight. The samples were knife milled to pass through a 20 mesh screen but were not sieved. The dry milled solids were than subjected to the acid hydrolysis procedure at a 50 mg solids scale. The solids were not first extracted with water or ethanol. HPLC analysis of sugars was done on an Aminex HPX-87H column and no analysis of lignin was attempted.

The soluble sugars glucose, cellobiose, and xylose in saccharification liquor were measured by HPLC (Waters Alliance Model, Milford, Mass.) using Bio-Rad HPX-87H column (Bio-Rad Laboratories, Hercules, Calif.) with appropriate guard columns, using 0.01 N aqueous sulfuric acid as the eluant. The sample pH was measured and adjusted to 5-6 with sulfuric acid if necessary. The sample was then passed through a 0.2 µm syringe filter directly into an HPLC vial. The HPLC run conditions were as follows:

Biorad Aminex HPX-87H (for carbohydrates):
Injection volume: 10-50 µL, dependent on concentration and detector limits
Mobile phase: 0.01 N aqueous sulfuric acid, 0.2 micron filtered and degassed
Flow rate: 0.6 mL/minute
Column temperature: 50° C., guard column temperature <60° C.
Detector temperature: as close to main column temperature as possible
Detector: refractive index
Run time: 15 minute data collection After the run, concentrations in the sample were determined from standard curves for each of the compounds.

EXAMPLES

General Procedure For Pretreatment (Delignification) of Biomass through Sequential Base Treatment with Sodium Carbonate Followed by Sodium Hydroxide Examples 1 through 6

Biomass (corn cob) was suspended in an aqueous solution of the first base (sodium carbonate) in an amount indicated in Table 1. The solid to liquid ratio used (% solids loading, typically 10 to 25%) is indicated in the Table. The suspension was heated to reflux (110° C.) or as indicated in the Table with continuous agitation. After the specified time of heating, the second base (sodium hydroxide) was added as a solid and the reaction was continued at the reflux temperature for an additional 20 hours. The reaction mixture was allowed to cool to room temperature and filtered to separate the polysaccharide-enriched solid from the lignin-containing liquid. The solid was extensively washed with water to remove the excess base and the excess water was drained from the solid under vacuum. The resulting moist solid was collected and a sample dried at 80° C. for 24 h to determine the moisture content. The carbohydrate composition of the solid was determined by NREL methods.

General Procedure for Delignification of Biomass Using Only Sodium Hydroxide, Only Sodium Carbonate, or a Sodium Hydroxide-sodium Carbonate Mixture Comparative Examples A through G Biomass (corn cob) was suspended in an aqueous solution of the base (sodium hydroxide, or sodium carbonate, or a mixture of sodium hydroxide and sodium carbonate) in an amount indicated in Table 4. The solid to liquid ratio depended on the biomass and the particle size distribution, as smaller particles tend to retain a greater amount of water and is indicated in the Table (typically 10 to 25%). The suspension was heated to reflux (110° C.) or as indicated in the Table with continuous agitation. After heating for typically 24 h), the reaction mixture was allowed to cool to room temperature and filtered to separate the polysaccharide-enriched solid from the lignin-containing liquid. The solid was extensively washed with water to remove the excess base and the excess water was drained from the solid under vacuum. The resulting moist solid was collected and a sample dried at 80° C. for 24 h to determine the moisture content. The carbohydrate composition of the solid was determined by NREL methods.

Enzymatic Saccharification

For all of the Examples and the Comparative Examples, the polysaccharide-enriched solid (delignified biomass) samples obtained using the procedures above were used for saccharification in order to determine the yield of glucose and xylose monomers through enzymatic saccharification, and the overall yield of glucose and xylose monomers through both the delignification and saccharification steps. For each sample, a portion of the moist solid corresponding to 1 dry gram was combined with an aqueous solution of polyethylene glycol (0.100 mL, 0.5%, molecular weight 2000), Accellerase™ 1000 cellulase (0.093 mL, protein concentration 97 mg/mL) and Multifect® CX 12L enzyme (0.107 mL, protein concentration 56 mg/mL) and enough pH 5.0, 50 mmol sodium citrate buffer to bring the reaction solids loading to 13.5 weight %. The reaction was heated to 50° C. with good mixing. The reaction was continued at this temperature and pH. Samples were withdrawn at 96 h from the time of the enzyme addition. The sample was diluted (on a weight basis), filtered through 0.2 micron filter, and the filtrate was analyzed by HPLC as described in the General Methods for glucose, xylose, and cellobiose and compared to a standard aqueous solution glucose (8.8 mg/g), xylose (8.9 mg/g), and cellobiose (8.8 mg/g). From this, the saccharification yield was calculated.

Table 1 provides the delignification conditions used, the compositions of the polysaccharide-enriched solids obtained, and the yields of solid (mass), glucan, and xylan through delignification for Examples 1-6 and Comparative Examples A-C. The yield of glucose and xylose monomers obtained through the saccharification step for Examples 1-6 and Comparative Examples A-C are shown in Table 2. The overall yield of glucose and xylose monomers through both delignification and saccharification for Examples 1-6 and Comparative Examples A-C are shown in Table 3.

TABLE 2

Yield of Glucose and Xylose Monomers Obtained in the 4 Day Enzymatic Saccharification of Delignified Cob Shown in Table 1.
SACCHARIFICATION PERCENT YIELD AFTER 4 d

| Example | Delignification Conditions | Monomers | |
|---|---|---|---|
| | | Glucose | Xylose |
| Comp. Ex. A | 8% NaOH at 0 h @ 110° C. | 92.5 | 89.4 |
| Comp. Ex. B | 8% Na$_2$CO$_3$ at 0 h @ 110° C. | 77.4 | 63.3 |
| 1 | 8.6% Na$_2$CO$_3$ at 0 h + 1.1% NaOH at 4 h @ 110° C. | 82.1 | 72.6 |
| 2 | 8.6% Na$_2$CO$_3$ at 0 h + 2% NaOH at 4 h @ 110° C. | 83.0 | 77.8 |
| 3 | 8.6% Na$_2$CO$_3$ at 0 h + 4.4% NaOH at 4 h @ 110° C. | 89.0 | 81.2 |
| 4 | 8.7% Na$_2$CO$_3$ at 0 h + 6.6% NaOH at 4 h @ 110° C. | 86.0 | 83.5 |
| 5 | 5% Na$_2$CO$_3$ at 0 h + 2% NaOH at 4 h @ 110° C. | 80.4 | 64.6 |
| 6 | 5% Na$_2$CO$_3$ at 0 h + 4% NaOH at 4 h @ 110° C. | 90.1 | 78.4 |
| Comp. Ex. C | 4% NaOH at 0 h + 5% Na$_2$CO$_3$ at 4 h @ 110° C. | 81.6 | 70.2 |

TABLE 3

Overall Yield (Delignification and Saccharification) of Glucose and Xylose Monomers Obtained in the 4 Day Enzymatic Saccharification of Delignified Corn Cob Shown in Table 1.
OVERALL PERCENT YIELD AFTER 4 d

| Example | Delignification Conditions | Monomers | |
|---|---|---|---|
| | | Glucose | Xylose |
| Comp. Ex. A | 8% NaOH at 0 h @ 110° C. | 73.0 | 73.4 |
| Comp. Ex. B | 8% Na$_2$CO$_3$ at 0 h @ 110° C. | 65.4 | 62.7 |

TABLE 1

Reaction Conditions, Solid Compositions, and Yields Obtained in Delignification with Sequential Addition of Sodium Carbonate Followed by Sodium Hydroxide, and with Comparative Base Treatments (Comparative Examples A, B, and C).

| Example | Delignification Conditions* | | Solids Loading | T [° C.] | Solid Composition | | | % Recovery in Solid*** | | |
|---|---|---|---|---|---|---|---|---|---|---|
| | 0 h | 4 h | | | Glucan | Xylan | Total Polysaccharide** | Mass | Glucan | Xylan |
| Raw Corn Cob | — | — | — | — | 38% | 30% | 68% | — | — | — |
| Comp. Ex. A | 8% NaOH | — | 25.00% | 110 | 49% | 39% | 88% | 60% | 80% | 82% |
| Comp. Ex. B | 8% Na$_2$CO$_3$ | — | 19.30% | 110 | 39% | 35% | 74% | 81% | 95% | 95% |
| 1 | 8.6% Na$_2$CO$_3$ | 1.1% NaOH | 15.70% | 110 | 43% | 36% | 79% | 75% | 90% | 86% |
| 2 | 8.6% Na$_2$CO$_3$ | 2.0% NaOH | 15.10% | 110 | 48% | 37% | 85% | 75% | 98% | 86% |
| 3 | 8.6% Na$_2$CO$_3$ | 4.4% NaOH | 15.30% | 110 | 48% | 38% | 86% | 69% | 90% | 83% |
| 4 | 8.7% Na$_2$CO$_3$ | 6.6% NaOH | 16.50% | 110 | 51% | 39% | 90% | 65% | 86% | 77% |
| 5 | 5.0% Na$_2$CO$_3$ | 2.0% NaOH | 18.80% | 110 | 39% | 35% | 74% | 82% | 93% | 94% |
| 6 | 5.0% Na$_2$CO$_3$ | 4.0% NaOH | 20.10% | 110 | 43% | 36% | 79% | 77% | 89% | 92% |
| Comp. Ex. C | 4.0% NaOH | 5.0% Na$_2$CO$_3$ | 17.30% | 110 | 40% | 37% | 77% | 75% | 79% | 92% |

*The amount of base used to prepare each material was measured in relation to the dry mass of the raw cellulosic biomass used in the given preparation.
**The sum of % glucan and % xylan in the solid composition obtained from pretreatment.
***The yields of mass, glucan, and xylan of the solid obtained from pretreatment, based on the mass and composition of the raw corn cob used in each Example, and in Comparative Examples A, B, and C.

TABLE 3-continued

Overall Yield (Delignification and Saccharification) of Glucose
and Xylose Monomers Obtained in the 4 Day Enzymatic
Saccharification of Delignified Corn Cob Shown in Table 1.
OVERALL PERCENT YIELD AFTER 4 d

| | | Monomers | |
|---|---|---|---|
| Example | Delignification Conditions | Glucose | Xylose |
| 1 | 8.6% $Na_2CO_3$ at 0 h + 1.1% NaOH at 4 h @ 110° C. | 70.4 | 68.1 |
| 2 | 8.6% $Na_2CO_3$ at 0 h + 2% NaOH at 4 h @ 110° C. | 79.3 | 74.9 |
| 3 | 8.6% $Na_2CO_3$ at 0 h + 4.4% NaOH at 4 h @ 110° C. | 78.6 | 74.1 |
| 4 | 8.7% $Na_2CO_3$ at 0 h + 6.6% NaOH at 4 h @ 110° C. | 75.8 | 73.5 |
| 5 | 5% $Na_2CO_3$ at 0 h + 2% NaOH at 4 h @ 110° C. | 68.6 | 64.6 |
| 6 | 5% $Na_2CO_3$ at 0 h + 4% NaOH at 4 h @ 110° C. | 79.4 | 75.5 |
| Comp. Ex. C | 4% NaOH at 0 h + 5% $Na_2CO_3$ at 4 h @ 110° C. | 65.5 | 68.1 |

Table 4 provides the delignification conditions used, the compositions of the polysaccharide-enriched solids obtained, and the yield of solid (mass), glucan, and xylan through delignification for Comparative Examples D-G. The yield of glucose and xylose monomers obtained through the saccharification step for Comparative Examples D-G are shown in Table 5. The overall yield of glucose and xylose monomers through both delignification and saccharification for Comparative Examples D-G are shown in Table 6.

TABLE 5

Yield of Glucose and Xylose Monomers Obtained in the 4 Day
Enzymatic Saccharification of Delignified Corn Cob Shown in Table 4.
SACCHARIFICATION PERCENT YIELD AFTER 4 d

| Comparative | | Monomers | |
|---|---|---|---|
| Example | Delignification Conditions | Glucose | Xylose |
| D | 5% $Na_2CO_3$ + 4% NaOH at 0 h @ 100° C. | 79.1 | 67.2 |
| E | 5% $Na_2CO_3$ + 4% NaOH at 0 h @ 140° C. | 77.2 | 71.8 |
| F | 5% $Na_2CO_3$ + 4% NaOH at 0 h @ 160° C. | 71.8 | 70.0 |
| G | 5% $Na_2CO_3$ + 4% NaOH at 0 h @ 170° C. | 76.6 | 68.5 |

TABLE 6

Overall Yield (Delignification and Saccharification) of Glucose
and Xylose Monomers Obtained in the 4 Day Enzymatic
Saccharification of Delignified Corn Cob Shown in Table 4.
OVERALL PERCENT YIELD AFTER 4 d

| Comparative | | Monomers | |
|---|---|---|---|
| Example | Delignification Conditions | Glucose | Xylose |
| D | 5% $Na_2CO_3$ + 4% NaOH at 0 h @ 100° C. | 74.1 | 66.3 |
| E | 5% $Na_2CO_3$ + 4% NaOH at 0 h @ 140° C. | 66.7 | 57.2 |

TABLE 4

Reaction Conditions, Solid Compositions, and Yields Obtained in Delignification with a Mixture of
Sodium Hydroxide and Sodium Carbonate (Comparative Examples - No Sequential Addition of Base).

| | Delignification Conditions* | | | Solid Composition | | | % Recovery in Solid*** | | |
|---|---|---|---|---|---|---|---|---|---|
| Comparative Example | Reagents added at 0 h | Solids Loading | T [° C.] | Glucan | Xylan | Total Polysaccharide** | Mass | Glucan | Xylan |
| Raw Corn Cob | — | — | — | 38% | 30% | 68% | — | — | — |
| D | 5.0% $Na_2CO_3$ + 4% NaOH | 29.80% | 100 | 45% | 36% | 81% | 78% | 94% | 94% |
| E | 5.0% $Na_2CO_3$ + 4% NaOH | 18.10% | 140 | 49% | 34% | 83% | 67% | 86% | 76% |
| F | 5.0% $Na_2CO_3$ + 4% NaOH | 29.80% | 160 | 50% | 31% | 81% | 67% | 89% | 69% |
| G | 5.0% $Na_2CO_3$ + 4% NaOH | 29.80% | 170 | 47% | 30% | 77% | 66% | 83% | 66% |

*The amount of base used to prepare each material was measured in relation to the dry mass of the raw cellulosic biomass used in the given preparation.
**The sum of % glucan and % xylan in the solid composition obtained from pretreatment.
***The yields of mass, glucan, and xylan of the solid obtained from pretreatment, based on the mass and composition of the raw corn cob used in each Comparative Example.

TABLE 6-continued

Overall Yield (Delignification and Saccharification) of Glucose and Xylose Monomers Obtained in the 4 Day Enzymatic Saccharification of Delignified Corn Cob Shown in Table 4.

OVERALL PERCENT YIELD AFTER 4 d

| Comparative Example | Delignification Conditions | Monomers | |
|---|---|---|---|
| | | Glucose | Xylose |
| F | 5% Na$_2$CO$_3$ + 4% NaOH at 0 h @ 160° C. | 63.7 | 50.8 |
| G | 5% Na$_2$CO$_3$ + 4% NaOH at 0 h @ 170° C. | 63.7 | 47.6 |

The solid composition data in Tables 1 and 4 show enrichment in glucan and xylan of the delignified solids, relative to the composition of the raw corn cob feedstock. The xylan and glucan yields (% recovery in solid) in Table 1 show how much of the polysaccharides were recovered and not lost in the pretreatment step. For example, Example 2 shows 98% recovery of glucan and 86% recovery of xylan in the solid obtained from pretreatment, meaning that 2% of the glucan and 14% of the xylan in the raw corn cob was lost in the delignification with sequential base treatment. This can be compared to 20% and 18% losses of glucan and xylan respectively for Comparative Example A. As seen in Table 2, Examples 1-6 provide good yields of both glucose and xylose through saccharification, better than for the case of sodium carbonate alone (Comparative Example B) or for a mixture of sodium hydroxide and sodium carbonate with no sequential addition of bases (Comparative Examples D, E, F, and G). Comparative Example A, which uses only sodium hydroxide, provides somewhat better glucose and xylose yield through saccharification than Examples 1-6, but with a more expensive reagent than the sequential use of sodium carbonate and a lower concentration of sodium hydroxide. Likewise, as seen in Table 3, Examples 1-6 show overall yields of glucose and xylose through the base treatment (delignification) and saccharification steps to be generally higher than those for Comparative Examples D, E, F, and G; sodium carbonate alone (Comparative Example B), or the reverse base treatment with sodium hydroxide first, followed by sodium carbonate (Comparative Example C).

Table 1, in comparison to Table 4, illustrates the desirable combination of good polysaccharide enrichment and high recovery of both glucan and xylan in the solid. Example 2 shows 85% polysaccharide enrichment with 98% glucan and 86% xylan recovery in the solid obtained by sequential base pretreatment. Example 6 gives 79% polysaccharide enrichment with 89% glucose and 92% xylose recovery in the solid.

FIG. 1 is a graphical representation of the overall yields of glucose and xylose monomers through the delignification and saccharification steps of Comparative Examples A (sodium hydroxide alone) and B (sodium carbonate alone), and Examples 1, 2, 3, and 4. FIG. 1 shows graphically that the yields of the sequentially base-treated Examples is superior to those obtained by use of only a single base (Comparative Examples).

The invention claimed is:

1. A method for the production of a saccharification product, the method comprising:

a) providing a cellulosic feedstock comprising lignin;
b) contacting, in water, the feedstock of (a) with at least one metal carbonate at a time of 0 hour at a temperature of no more than 200° C. to produce a first delignification slurry;
c) contacting the first delignification slurry with a nucleophilic base at a concentration of no more than 8% on a mass basis at a time of at least 0+0.5 hour and at a temperature of no more than 200° C. to form a second delignification slurry comprising a lignin-containing liquid fraction and a polysaccharide-enriched solid fraction;
d) separating the lignin-containing liquid fraction from the polysaccharide-enriched solid fraction; and
e) contacting at least a portion of the polysaccharide-enriched solid fraction with an enzyme consortium to produce a saccharification product comprising xylose and glucose monomers wherein the overall yield of xylose and glucose monomers in the saccharification product are individually at least about 50%; wherein said enzyme consortium consists essentially of cellulases and xylanases and wherein saccharification occurs under the conditions of a pH of about 4.5 to about 5.7 and a temperature of about 45° C. to about 55° C.

2. The method of claim 1 wherein the cellulosic feedstock is selected from the group consisting of switchgrass, corn grain, corn cobs, corn husks, corn stover, grasses, wheat, wheat straw, hay, barley, barley straw, rice straw, sugar cane bagasse, sorghum, soy, components obtained from processing of grains, trees, branches, roots, leaves, wood chips, sawdust, shrubs and bushes, vegetables, fruits, flowers, and animal manure, and a combination of these.

3. The method of claim 1 wherein the nucleophilic base comprises a soluble metal hydroxide.

4. The method of claim 3 wherein the nucleophilic base is selected from the group consisting of lithium hydroxide, sodium hydroxide, potassium hydroxide, cesium hydroxide, magnesium hydroxide, and combinations thereof.

5. The method of claim 1 wherein the metal carbonate is selected from the group consisting of lithium carbonate, sodium carbonate, potassium carbonate, cesium carbonate, magnesium carbonate, ammonium carbonate, and combinations thereof.

6. The method of claim 1 wherein the contacting of step (c) is at a time of between 0.5 and 20 hours inclusive.

7. The method of claim 1 wherein the ratio of the concentration of nucleophilic base to the concentration of metal carbonate in the second delignification slurry of step (c) is from about 0.1:1 to about 1.0:1 on a weight basis.

8. The method of claim 1 wherein the initial reaction conditions include an initial pH range from about 9.0 to about 11.0 and a reaction temperature of about 30° C. to about 200° C.

9. The method of claim 1 wherein the secondary reaction conditions include a reaction temperature of about 25° C. to about 200° C.

10. The method of claim 1 wherein the lignin-containing liquid fraction is pyrolyzed to form a metal carbonate-containing ash.

11. The method claim 1 wherein the metal carbonate of step (b) is supplied by the metal carbonate-containing ash of claim 10.

* * * * *